US00PP34900P2

(12) United States Plant Patent
van Diepen

(10) Patent No.: US PP34,900 P2
(45) Date of Patent: Jan. 3, 2023

(54) ***PRIMULA* PLANT NAMED 'IFPROB'**

(50) Latin Name: *Primula vulgaris*
Varietal Denomination: IFPROB

(71) Applicant: INNOFLORA PLANT BREEDING B.V., Heerhugowaard (NL)

(72) Inventor: Arie van Diepen, Hoogwoud (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/875,347

(22) Filed: Jul. 27, 2022

(51) Int. Cl.
*A01H 5/02* (2018.01)
*A01H 6/00* (2018.01)

(52) U.S. Cl.
USPC ..... Plt./472
CPC ..... *A01H 6/00* (2018.05)

(58) Field of Classification Search
USPC ..... Plt./472
CPC ..... A01H 5/02
See application file for complete search history.

*Primary Examiner* — Kent L Bell
(74) *Attorney, Agent, or Firm* — C. Anne Whealy

(57) ABSTRACT

A new and distinct *Primula* plant named 'IFPROB', characterized by its compact and upright plant habit; moderately vigorous to vigorous growth habit and moderate growth rate; dense basal rosettes of leaves with inflorescences held above the foliar plane; freely flowering habit; violet-colored flowers with bright yellow-colored centers; and good garden performance.

2 Drawing Sheets

Figure 1:
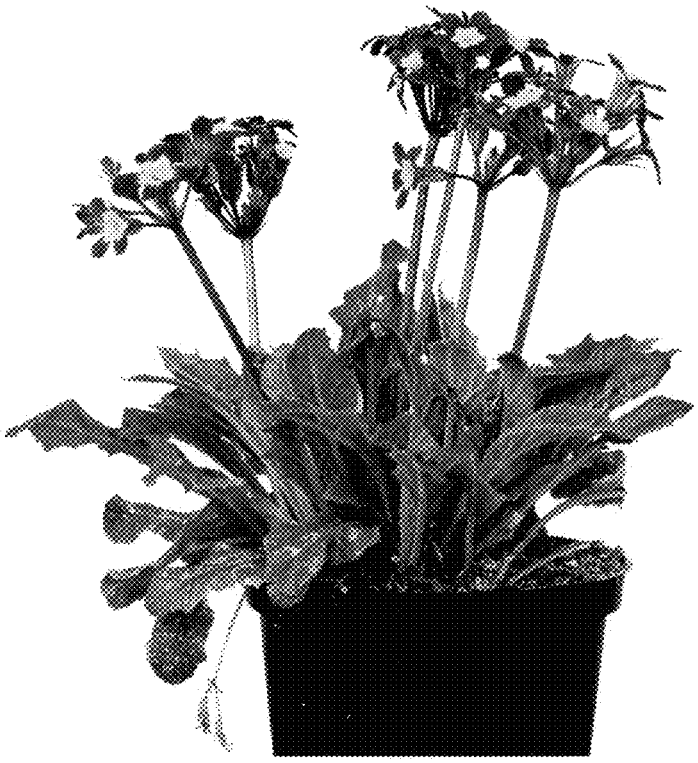

Botanical designation: *Primula vulgaris*.
Cultivar denomination: 'IFPROB'.

BACKGROUND OF THE INVENTION

The present invention relates to a new and distinct cultivar of *Primula* plant, botanically known as *Primula vulgaris*, commonly referred to as Primrose and hereinafter referred to by the name 'IFPROB'.

The new *Primula* plant is a product of a planned breeding program conducted by the Inventor in Heerhugowaard, The Netherlands. The objective of the breeding program is to create new compact and uniformly mounding *Primula* plants with numerous attractive flowers and good garden performance.

The new *Primula* plant originated from a cross-pollination made by the Inventor in April, 2017 in Heerhugowaard, The Netherlands of a proprietary selection of *Primula vulgaris* identified as code number 13-58-02, not patented, as the female or seed parent, with a proprietary selection of *Primula vulgaris* identified as code number 12-13-01, not patented, as the male or pollen parent. The new *Primula* plant was discovered and selected by the Inventor as a single flowering plant within the progeny of the stated cross-pollination in a controlled greenhouse environment in Heerhugowaard, The Netherlands in April, 2018.

Asexual reproduction of the new *Primula* plant by in vitro meristem culture in a controlled greenhouse environment in Heerhugowaard, The Netherlands since June, 2019 has shown that the unique features of this new *Primula* plant are stable and reproduced true to type in successive generations.

SUMMARY OF THE INVENTION

Plants of the new *Primula* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFPROB'. These characteristics in combination distinguish 'IFPROB' as a new and distinct *Primula* plant:

1. Compact and upright plant habit.
2. Moderately vigorous to vigorous growth habit and moderate growth rate.
3. Dense basal rosettes of leaves with inflorescences held above the foliar plane.
4. Freely flowering habit.
5. Violet-colored flowers with bright yellow-colored centers.
6. Good garden performance.

Plants of the new *Primula* can be compared to plants of the female parent selection. In side-by-side comparisons, plants of the new *Primula* differ primarily from plants of the female parent selection in the following characteristics:

1. Plants of the new *Primula* are more compact than plants of the female parent selection.
2. Plants of the new *Primula* have smaller flowers than plants of the female parent selection.

Plants of the new *Primula* can be compared to plants of the male parent selection. In side-by-side comparisons, plants of the new *Primula* differ primarily from plants of the male parent selection in the following characteristics:

1. Plants of the new *Primula* have larger flowers than plants of the male parent selection.
2. Flowers of plants of the new *Primula* are violet and bright yellow in color whereas flowers of plants of the male parent selection are red and yellow in color.

Plants of the new *Primula* can be compared to plants of *Primula vulgaris* 'Oakleaf Yellow', not patented. In side-by-side comparisons, plants of the new *Primula* differ primarily from plants of 'Oakleaf Yellow' in the following characteristics:

1. Plants of the new *Primula* are more compact than plants of 'Oakleaf Yellow'.
2. Plants of the new *Primula* flower for a shorter period of time than plants of 'Oakleaf Yellow'.
3. Plants of the new *Primula* have smaller flowers than plants of 'Oakleaf Yellow'.
4. Flowers of plants of the new *Primula* are violet and bright yellow in color whereas flowers of plants of 'Oakleaf Yellow' are red and yellow in color.

BRIEF DESCRIPTION OF THE PHOTOGRAPHS

The accompanying colored photographs illustrate the overall appearance of the new *Primula* plant showing the colors as true as it is reasonably possible to obtain in colored reproductions of this type. Colors in the photographs may differ slightly from the color values cited in the detailed botanical description which accurately describe the colors of the new *Primula* plant.

The photograph on the first sheet (FIG. 1) is a side perspective view of a typical flowering plant of 'IFPROB' grown in a container.

Figure 2:
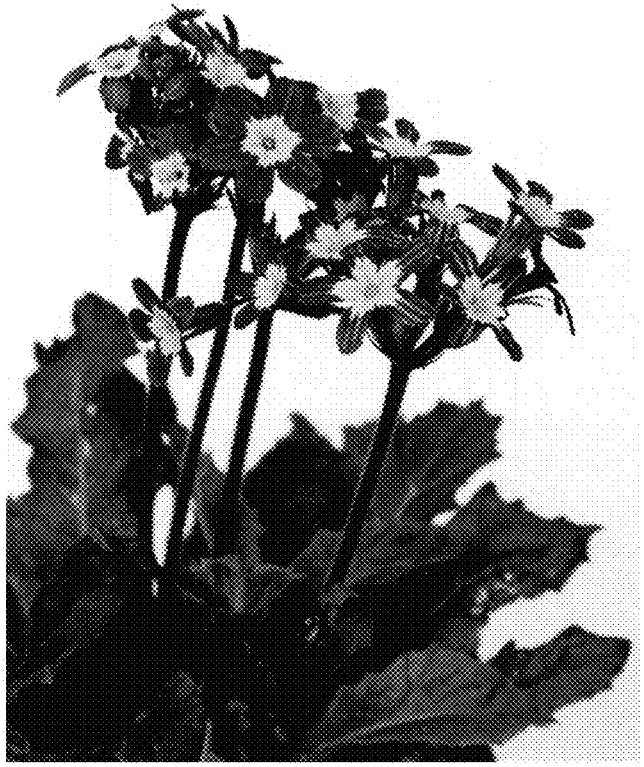

The photograph at the top of the second sheet (FIG. 2) is a close-up view of a typical flowering plant of 'IFPROB'.

Figure 3:
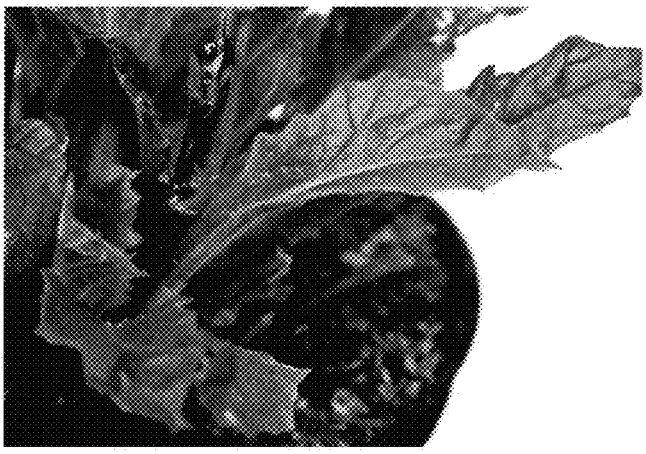

The photograph at the bottom of the second sheet (FIG. 3) is a close-up view of typical leaves of 'IFPROB'.

DETAILED BOTANICAL DESCRIPTION

The aforementioned photographs and following observations and measurements describe plants grown during the spring in 1.5-liter containers in an outdoor nursery in Heerhugowaard, The Netherlands and under cultural practices typical of commercial *Primula* production. During the production of the plants, day temperatures ranged from 10° C. to 20° C. and night temperatures ranged from 10° C. to 13° C. Plants were 18 weeks from planting when the photographs and description were taken. In the following description, color references are made to The Royal Horticultural Society Colour Chart, 2015 Edition, except were general terms of ordinary dictionary significance are used.

Botanical classification: *Primula vulgaris* 'IFPROB'.

Parentage:

*Female, or seed, parent*.—Proprietary selection of *Primula vulgaris* identified as code number 13-58-02, not patented.

*Male, or pollen, parent*.—Proprietary selection of *Primula vulgaris* identified as code number 12-13-01, not patented.

Propagation:

*Type*.—In vitro meristem culture.

*Time to initiate roots, summer*.—About ten days at temperatures about 22° C.

*Time to initiate roots, winter*.—About 15 days at temperatures about 20° C.

*Time to produce a rooted plant, summer*.—About 42 days at temperatures about 20° C.

*Time to produce a rooted plant, winter*.—About 50 days at temperatures about 20° C.

*Root description*.—Fine, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; relatively compact and upright plant habit; overall plant shape, ovate to broadly oblong; dense basal rosette of leaves with inflorescences held above the foliar plane; moderately vigorous to vigorous growth habit and moderate growth rate.

*Plant height, soil level to top of foliar plane*.—About 12.4 cm.

*Plant height, soil level to top of floral plane*.—About 20.4 cm.

*Plant diameter* (*area of spread*).—About 24.1 cm.

Leaf description:

*Arrangement*.—In a basal rosette; simple; about 63 leaves per plant at one time.

*Length*.—About 10.6 cm.

*Width*.—About 4.1 cm.

*Shape*.—Oblanceolate to narrowly obovate.

*Apex*.—Long and narrowly acuminate.

*Base*.—Obtuse.

*Margin*.—Irregularly dentate to shallowly runcinate; moderately undulate.

*Aspect*.—About 30° to 70° from soil level; slightly to moderately carinate.

*Texture and luster, upper surface*.—Densely pubescent; slightly velvety; not rugose; slightly glossy.

*Texture and luster, lower surface*.—Densely pubescent; slightly rugose; matte.

*Venation pattern*.—Anastomosing.

*Color*.—Developing leaves, upper surface: Close to 143A to slightly darker than 143A. Developing leaves, lower surface: Close to 143B. Fully developed leaves, upper surface: Close to 137B; venation, close to 146D. Fully developed leaves, lower surface: Close to a blend of 146B and 147B; venation, close to 145A to 145B.

*Petioles*.—Length: About 3.7 cm. Diameter, flattened: About 3 mm by 5.5 mm. Strength: Moderately strong to strong. Texture and luster, upper and lower surfaces: Pubescent; moderately glossy. Color, upper surface: Close to 144B; margins, close to 146A; at the base, close to 185C. Color, lower surface: Close to 145A; margins, close to 146A; at the base, close to 185B.

Flower description:

*Flower type and flowering habit*.—Rotate salverform flowers arranged in umbels; freely flowering habit with about twelve flowers per inflorescence and about 60 flowers developing per plant; flowers face mostly upright to slightly outwardly.

*Natural flowering season*.—Plants flower during the spring in The Netherlands.

*Flower longevity on the plant*.—About two weeks; flowers persistent.

*Fragrance*.—None detected.

*Flower buds*.—Length: About 1.5 cm. Diameter: About 5 mm. Shape: Oblong. Texture and luster: Densely pubescent; matte. Color: Immature sepals, close to 144D with midvein and apices, close to 177A; immature petals, close to N88A.

*Inflorescence height*.—About 4.6 cm.

*Inflorescence diameter*.—About 8.2 cm.

*Flower diameter*.—About 3.5 cm.

*Flower depth* (*height*).—About 2 cm.

*Throat diameter*.—About 2.5 mm.

*Tube length*.—About 1.5 cm.

*Tube diameter*.—About 3 mm.

*Petals*.—Quantity and arrangement: Five, or occasionally six, petals fused in a single salverform whorl; lower 50% of the petals is fused. Petal lobe length (from throat): About 3 cm. Petal lobe width: About 9 mm to 12 mm. Petal lobe shape: Spatulate. Petal lobe apex: Shallowly emarginate to shallowly praemorse. Petal lobe margin: Entire; not undulate. Petal lobe texture and luster, upper and lower surfaces: Smooth, glabrous; velvety; not rugose; matte. Throat texture and luster: Smooth, glabrous; slightly velvety; matte. Tube texture and luster: Moderately pubescence; matte. Color: When opening, upper surface: Close to 86A to darker than 86A; towards the center, close to 6A. When opening, lower surface: Close to a blend of N79A and 83A; towards the base, close to N82B and N82C. Fully opened, upper surface: Close to 86A and 86B; towards the center, close to 12A; venation, close to 86A to darker than 86A; with subsequent development, main color becoming closer to 86C with venation, close to 86A to 86B. Fully opened, lower surface: Close to 86A; towards the base, close to N77B; venation, close to 86A to darker than 86A; with subsequent development, color becoming closer to 86C with venation, close to 86A and towards the base, close to N78B. Flower throat (inside): Close to 12A; venation, close to 12A; towards the base, close to N144B and at the base, close to 182B. Flower tube (outside): Close to 163C; towards the base, close to 182A; venation, similar to lamina colors.

*Sepals*.—Quantity and arrangement: Five, or occasionally six, sepals fused in a single whorl; lower 37.5% of the sepals is fused; calyx, narrowly campanulate in shape. Length: About 1.5 cm. Width: About 3 mm. Shape: Lanceolate. Apex: Narrowly acuminate. Margin: Entire. Texture and luster, upper surface: Smooth, glabrous; matte. Texture and luster, lower surface: Densely pubescent; matte. Color: When opening, upper surface: Close to 145A; narrow apical margins, close to 177A. When opening, lower surface: Close to 144D; midvein and apices, close to 177A. Fully opened, upper surface: Close to 144B; narrow apical margins, close to 166A. Fully opened, lower surface: Close to 144A; midvein and apices, close to 166A.

*Peduncles*.—Length: About 15.9 cm. Width: About 3 mm. Strength: Moderately strong. Angle: Erect to about 15° from vertical. Texture and luster: Densely pubescent; glossy. Color: Close to 200C; distally, tinged with close to N79A.

*Pedicels*.—Length: About 2.5 cm. Width: About 1.5 mm. Strength: Moderately strong. Angle: Erect to about 25° from peduncle axis. Texture and luster: Densely pubescent; moderately glossy. Color: Close to 177A; proximally, tinged with close to 183B.

*Floral bracts*.—Quantity and arrangement: One at the base of the pedicel. Length: About 1.1 cm. Width: About 1 mm. Shape: Linear. Texture, upper surface: Smooth, glabrous. Texture, lower surface: Moderately pubescent. Color, upper surface: Close to 138C. Color, lower surface: Close to 200A to 200B.

*Reproductive organs*.—Stamens: Quantity per flower: About five. Filament length: About 0.5 mm. Filament color: Close to 155A. Anther size: About 0.5 mm by 1 mm. Anther shape: Oblong; basifixed. Anther color: Close to 14C. Pollen amount: Moderate. Pollen color: Close to 12A. Pistils: Quantity per flower: One. Pistil length: About 1.1 cm. Style length: About 1 cm. Style color: Close to 145C. Stigma diameter: About 1 mm. Stigma shape: Club-shaped. Stigma color: Close to N144B. Ovary color: Close to 144B.

*Seeds and fruits*.—To date, seed and fruit development has not been observed on plants of the new *Primula*.

Pathogen & pest resistance: To date, plants of the new *Primula* have not been noted to be resistant to pathogens or pests common to *Primula* plants.

Garden performance: Plants of the new *Primula* have been observed to have good garden performance and have been observed to tolerate rain, wind and temperatures ranging from about −5° C. to about 35° C. Plants of the new *Primula* are suitable for U.S.D.A. Hardiness Zones 8 to 10.

It is claimed:

1. A new and distinct *Primula* plant named 'IFPROB' as illustrated and described.

* * * * *